United States Patent
Chen et al.

(10) Patent No.: US 10,399,919 B2
(45) Date of Patent: Sep. 3, 2019

(54) METHOD FOR PREPARING PHENOL

(71) Applicant: Changzhou University, Changzhou (CN)

(72) Inventors: Qun Chen, Changzhou (CN); Xuan Dai, Changzhou (CN); Weiyou Zhou, Changzhou (CN); Fu'an Sun, Changzhou (CN); Mingyang He, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 15/953,864

(22) Filed: Apr. 16, 2018

(65) Prior Publication Data
US 2019/0062245 A1   Feb. 28, 2019

(30) Foreign Application Priority Data

Aug. 28, 2017 (CN) .......................... 2017 1 0747673

(51) Int. Cl.
*C07C 37/08* (2006.01)
*B01J 19/00* (2006.01)

(52) U.S. Cl.
CPC .......... *C07C 37/08* (2013.01); *B01J 19/0093* (2013.01); *B01J 2219/0086* (2013.01); *B01J 2219/00873* (2013.01); *B01J 2219/00889* (2013.01); *Y02P 20/52* (2015.11)

(58) Field of Classification Search
CPC .......... C07C 37/08; B01J 19/003; Y02P 20/52

USPC ....................................................... 568/798
See application file for complete search history.

(56) References Cited

FOREIGN PATENT DOCUMENTS

WO           2010037912           4/2010

*Primary Examiner* — Deborah D Carr
(74) *Attorney, Agent, or Firm* — Porzio Bromberg & Newman P.C.

(57) ABSTRACT

The present invention relates to the technical field of peroxide decomposition, and discloses a method for preparing phenol, which comprises the following steps: (1) mixing cumene hydroperoxide and liquid acid or solid acid with a solvent to form a homogeneous solution or uniformly dispersed system; (2) loading the homogeneous solution or uniformly dispersed system of cumene hydroperoxide with a homogeneous solution or uniformly dispersed system of acid into a preheating module and preheating in a microchannel continuous flow mode, preliminarily mixing the preheated materials for reaction in a mixing module in a micro-channel continuous flow mode, and then further mixing the materials for reaction in a series of mixing and reaction module groups in a micro-channel continuous flow mode, to obtain phenol. The method provided in the present invention is easy, simple and safe to operate, can implement continuous production of phenol product at a high yield ratio; in addition, since the reaction in the present invention is a cracking reaction, which releases heat strongly, the safety factor of the process is significantly improved owing to the strong heat release characteristic in conjunction with the unique heat transfer property of the micro-channels. With the method provided in the present invention, the yield of the product is higher than 99%.

20 Claims, 2 Drawing Sheets

METHOD FOR PREPARING PHENOL

CROSS REFERENCE TO RELATED APPLICATIONS

This application claims priority to Chinese Application No. 201710747673.7, filed on Aug. 28, 2017, entitled "a method for preparing phenol utilizing a micro-channel reactor", which is specifically and entirely incorporated by reference.

FIELD OF THE INVENTION

The present invention relates to the technical field of peroxide decomposition, in particular to a method for preparing phenol utilizing a micro-channel reactor.

BACKGROUND OF THE INVENTION

Phenol, with a common name as carbolic acid, is a raw material widely applied in the organic chemical industry, and is mainly used to produce phenolic resin, caprolactam, bisphenol A, adipic acid, phenylamine, alkyl phenol, and salicylic acid, etc. In addition, it can also be used as a solvent or disinfectant, and is widely applied in production of synthetic fibers, synthetic rubbers, plastic materials, medicines, pesticides, spices, dyes, and paints, etc.

At present, processes for phenol production in industries and researches mainly include: sulfonation process, methyl benzene-benzoic acid process, chlorobenzene hydrolysis process, direct benzene oxidation process, sec.-butylbenzene process, and cumene process, etc.

(1) Sulfonation Process

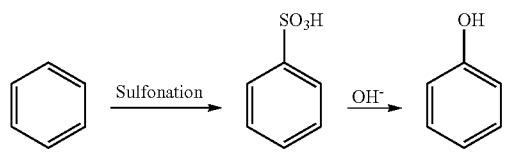

Process characteristics: This process involves complex reaction and cause severe corrosion of equipment and high maintenance cost, doesn't support continuous production, and results in severe environmental pollution and a large number of byproducts.

(2) Methyl Benzene-Benzoic Acid Process

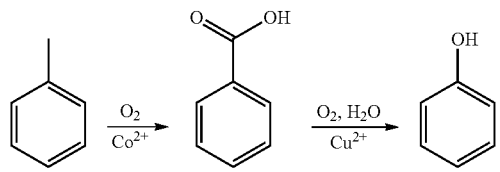

Process characteristics: The process is simple, doesn't have strict requirements for raw materials, achieves high reaction yield and high selectivity, is free of environmental protection, and realizes comprehensive utilization of energy. However, tar may be generated easily in the process and has impact on product yield and catalyst life; in addition, a great deal of heat is released in the reaction process and may cause explosion.

(3) Chlorobenzene Hydrolysis Process

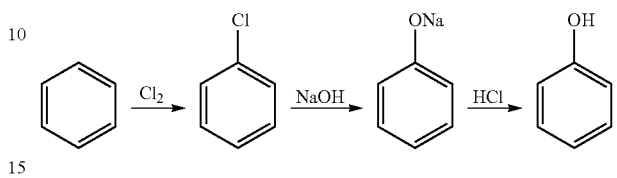

Process characteristics: This process is simple, the byproducts can be separated easily, the production scale can be large, but the process has strict requirements for operating conditions, the production equipment and materials must be acid-resistant and alkali-resistant, and the equipment investment is high because an electrolytic apparatus is required (for chloride electrolysis).

(4) Direct Benzene Oxidation Process

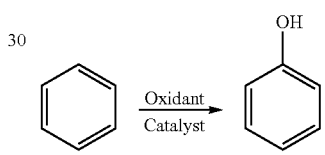

Process characteristics: This process has high performance in atom economy and is simple, achieves high product yield, and has very low environmental pollution; however, the electron cloud density of the product (phenol) is higher than that of the raw material (benzene), and high-valence oxidation that requires electrons may happen easily.

(5) Sec-Butylbenzene Process

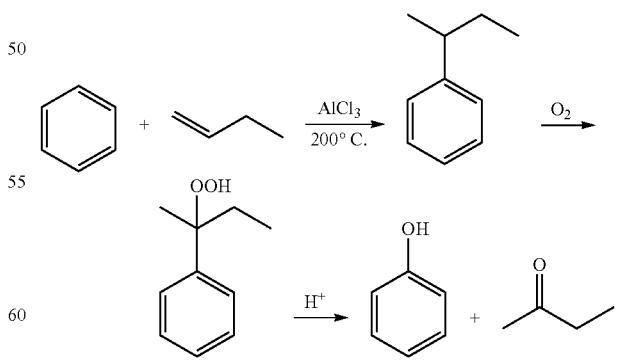

Process characteristics: This process produces less acetone byproduct and has lower production cost; however, most of the byproducts have boiling points close to each other and are difficult to separate from each other.

(6) Cumene Process

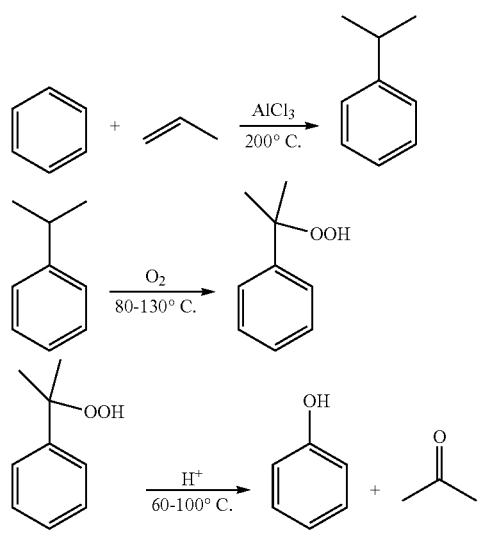

In this process, cumene is oxidized in a liquid phase to generate cumene hydroperoxide (CHP) first, and then the CHP is concentrated and decomposed through catalytic decomposition with sulfuric acid to obtain phenol and acetone. This method is the principal and the most important method for producing phenol product presently. Process characteristics: The quality of the product obtained through this process is good, the cost is lower, and the equipment corrosion and environmental pollution are less; however, the reaction is violent and releases great heat; therefore, a lot of material circulation is required to carry away the heat to prevent explosion; besides, owing to the strong acidity, oxidization and dehydration properties of sulfuric acid, the decomposition selectivity is low, and many byproducts (e.g., tar) are produced; moreover, the CHP raw material must be concentrated to reduce sulfuric acid consumption and decrease corrosiveness, causing increased operation hazards. In addition, in the intermittent reaction process, byproducts byproducts are increased owing to long detention time; furthermore, the reactor is large in size and occupies a large floor space in the workshop.

Up to now, no report on research of phenol preparation through acid catalytic decomposition of CHP in a micro-channel continuous flow mode has been found.

SUMMARY OF THE INVENTION

To overcome the drawbacks in the prior art, including difficulty in accurate control of reaction conditions, low reaction efficiency, poor process safety, and inability to continuous production, etc., the present invention provides a method for preparing phenol through acid catalytic decomposition of CHP in a micro-channel continuous flow mode.

To attain the object described above, in one aspect, the present invention provides a method for preparing phenol, which comprises the following steps:

(1) mixing cumene hydroperoxide and liquid acid or solid acid with a solvent to form a homogeneous solution or uniformly dispersed system;

(2) loading the homogeneous solution or uniformly dispersed system of cumene hydroperoxide with a homogeneous solution or uniformly dispersed system of acid into a preheating module and preheating in a micro-channel continuous flow mode, preliminarily mixing the preheated materials for reaction in a mixing module in a micro-channel continuous flow mode, and then further mixing the materials for reaction in a series of mixing and reaction module groups in a micro-channel continuous flow mode, to obtain phenol.

Compared with the prior art, the present invention attains the following beneficial effects:

(1) The method employs a micro-channel continuous flow reactor operating in a continuous flow mode, and thereby significantly shortens the reaction time and greatly improves reaction efficiency; remarkably reduce the hold-up liquid in the equipment, simplifies the operation flow, and avoids additional devices required in conventional intermittent operation.

(2) The reaction is smooth and steady, without temperature or pressure out-of-control phenomenon, and the potential safety hazards in existing processes are avoided.

(3) Since the CHP can have a decomposition reaction within a wide concentration range, the solvent consumption is greatly reduced.

(4) The CHP may be directly from a cumene oxidation liquid; therefore, the concentration procedure in the existing processes is omitted, the process is simplified, and the process safety is improved.

BRIEF DESCRIPTION OF THE SYMBOLS

Figure 2:
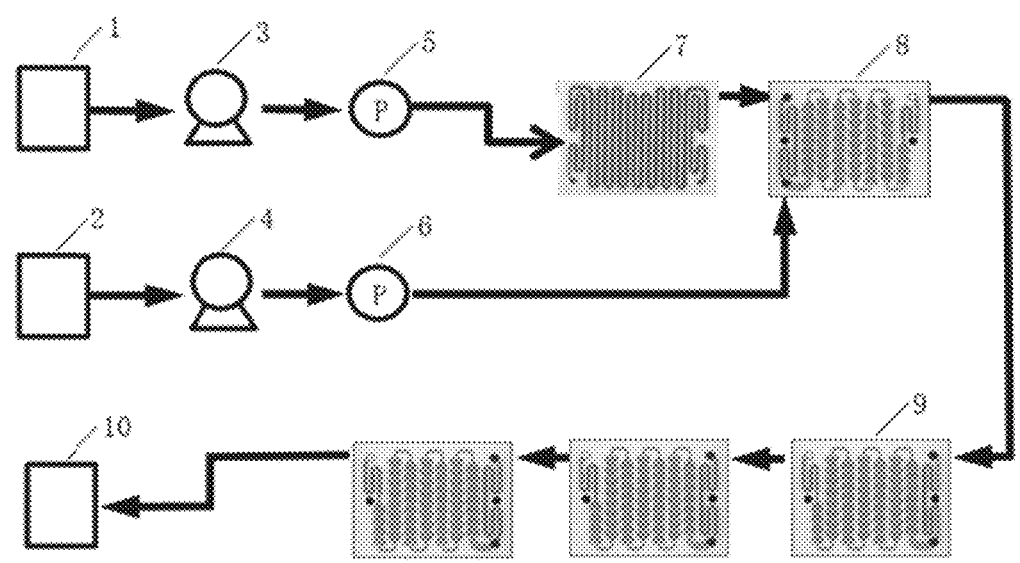
FIG. 2 is a reaction flow chart of the micro-channel reactor in embodiments 1 and 4-14.
Figure 3:
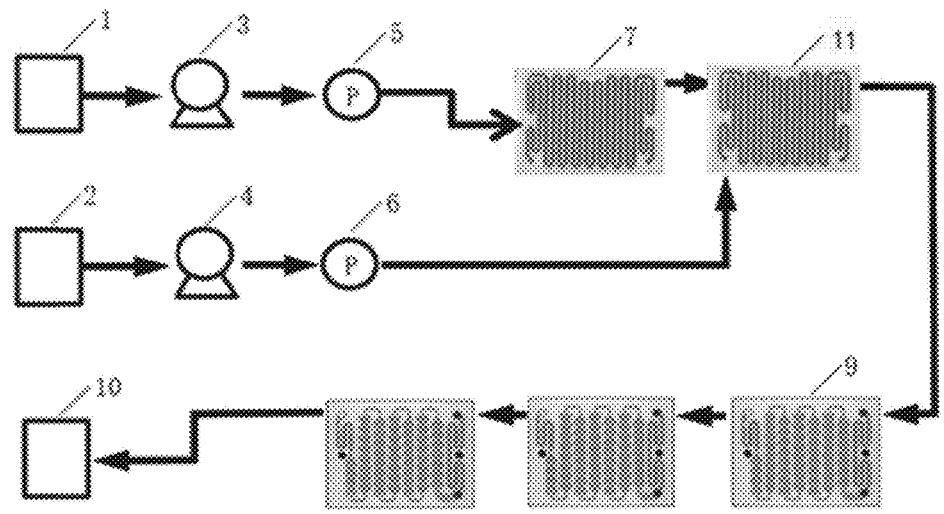
FIG. 3 is a reaction flow chart of the micro-channel reactor in embodiment 2.
Figure 4:
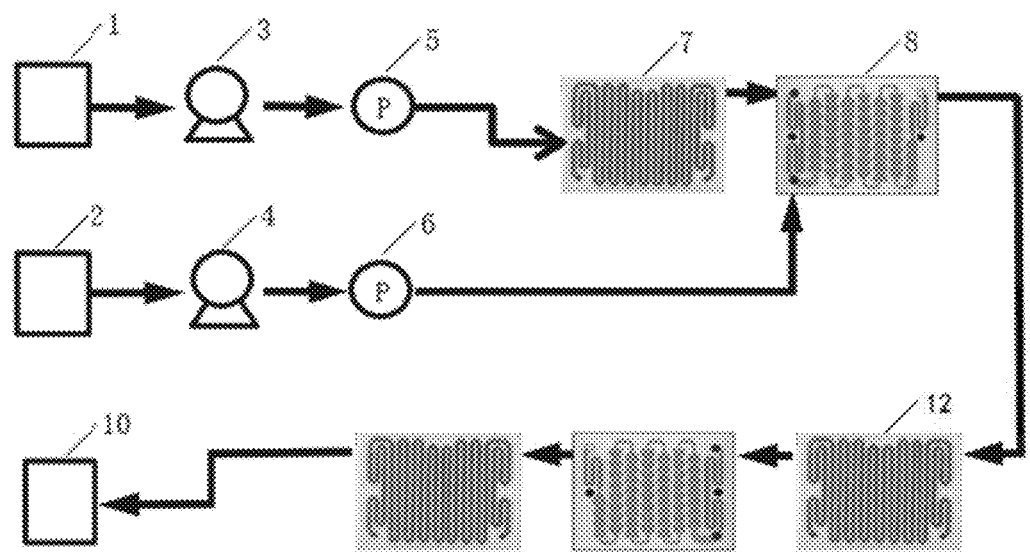
FIG. 4 is a reaction flow chart of the micro-channel reactor in embodiment 3.

In FIG. 2: 1, 2—feed tank; 3, 4—metering pump; 5, 6—pressure meter; 7—straight micro-channel module; 8—enhanced heart-shaped micro-channel module; 9—a series of enhanced heart-shaped micro-channel modules; 10—reaction liquid reservoir;

In FIG. 3: 11—straight micro-channel module; 9—a series of enhanced heart-shaped micro-channel modules;

In FIG. 4: 8—enhanced heart-shaped micro-channel module; 12—a series of enhanced heart-shaped micro-channel modules and straight micro-channel modules.

DETAILED DESCRIPTION OF THE EMBODIMENTS

The ends points and any value in the ranges disclosed in the present invention are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically in this document.

Hereunder some embodiments of the present invention will be detailed. It should be understood that the embodiments described here are only provided to describe and explain the present invention, but shall not be deemed as constituting any limitation to the present invention.

The present invention provides a method for preparing phenol, which comprises the following steps:

(1) mixing cumene hydroperoxide and liquid acid or solid acid (cumene hydroperoxide and liquid acid, or cumene hydroperoxide and solid acid) with a solvent to form a homogeneous solution or uniformly dispersed system;

(2) loading the homogeneous solution or uniformly dispersed system of cumene hydroperoxide with a homogeneous solution or uniformly dispersed system of acid into a preheating module and preheating in a micro-channel continuous flow mode, preliminarily mixing the preheated materials for reaction in a mixing module in a micro-channel continuous flow mode, and then further mixing the materials for reaction in a series of mixing and reaction module groups in a micro-channel continuous flow mode, to obtain phenol.

The present invention employs a high-flux micro-channel continuous flow reactor operating in a micro-channel continuous flow mode to prepare phenol through acid catalytic decomposition of CHP. The reaction conditions of the process can be controlled accurately to improve production safety; in addition, owing to continuous reaction, the reaction efficiency is improved significantly, the CHP transformation ratio is greatly improved in very short time, and the phenol selectivity is improved. Besides, with the micro-channel continuous flow reactor operating in a continuous flow mode, the hold-up liquid in the equipment is greatly reduced, the operation flow is simplified, additional devices required in conventional intermittent operation are avoided, the reaction is smooth and steady without temperature or pressure out-of-control phenomenon, and the potential safety hazards in existing processes are avoided.

According to the present invention, in the homogeneous solution or uniformly dispersed system of cumene hydroperoxide in the step (1), the mass concentration of cumene hydroperoxide is 10~60%; thus, the decomposition reaction can happen within a wide concentration range, and thereby the solvent consumption is remarkably reduced. Preferably, the mass concentration of cumene hydroperoxide is 15~48%.

In the present invention, the cumene hydroperoxide may be directly from a cumene oxidation liquid; thus, a concentration procedure in existing processes is omitted, the process is simplified, and the process safety is improved; alternatively, concentrated cumene hydroperoxide at 80% or higher concentration may be used.

In the present invention, to attain a better acid catalysis effect, in the homogeneous solution or uniformly dispersed system of liquid acid in the step (1), the molar concentration of the liquid acid is 1~35%. For example, the molar concentration may be any value among point values 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 33%, 34% and 35%, or any value within a range composed by any two of those point values. Preferably, the molar concentration of the liquid acid is 1.5~25%.

In the present invention, in the homogeneous solution or uniformly dispersed system of solid acid, the mass concentration of the solid acid in the step (1) is 2~15%. For example, the mass concentration may be any value among point values 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5% and 15%, or any value within a range composed of any two of those point values.

In the present invention, to attain a better acid catalysis effect, the liquid acid is at least one of sulfuric acid, methanesulfonic acid, and trifluoromethanesulfonic acid.

According to the present invention, the solid acid is a solid super-acid and/or zeolite, wherein the solid super-acid refers to acid with acidity higher than that of 100% sulfuric acid. For example, on the premise that the acidity is represented by a Hammett acidity function $H_o$, the $H_o$ value of 100% sulfuric acid is −11.93, and an acid with $H_o$<−11.93 is a super-acid. Solid super-acids are categorized into two categories: one category includes fluoride immobilized acids that contain halogens and perfluorinated resin; the other category of solid super-acids don't contain halogens; they are prepared from sulfate radicals absorbed on the surface of a metal oxide or hydroxide through high-temperature combustion, such as $WO_3/ZrO^{2-}$—$Fe_2O_3$. Zeolites have ion-exchange capability, pore canals in uniform molecular dimensions, and acid catalysis activity, activity, and have favorable thermostability and hydrothermal stability, such as $ZnCl_2/MCM$-41.

In the present invention, to obtain a better homogeneous solution or uniformly dispersed system, the solvent in the step (1) is acetone and/or cumene.

In the present invention, to improve the transformation ratio of CHP and the yield of phenol product, the molar ratio of cumene hydroperoxide to liquid acid in the step (2) is 10~1,500:1. For example, the molar ratio may be any value among point values 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1, 400:1, 450:1, 500:1, 550:1, 600:1, 650:1, 700:1, 750:1, 800:1, 850:1, 900:1, 950:1, 1,000:1,500:1, or any value within a range composed of any two of those point values; preferably, the molar ratio of cumene hydroperoxide to liquid acid is 200~1,000:1.

In the present invention, the mass ratio of cumene hydroperoxide to solid acid in the step (2) is 50~200:1. For example, the mass ratio may be any value among point values 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1 and 200:1, or any value within a range composed of any two of those point values.

In the present invention, to improve the transformation ratio of CHP and the yield of phenol product, ensure smooth and steady reaction, prevention a temperature or pressure out-of-control phenomenon and improve safety of the production process, in the mixing and reaction of the mixing and reaction module groups in step (2), the detention time of the material is controlled to be 10~400 s; for example, the detection time may be any value among point values 10 s, 20 s, 30 s, 40 s, 50 s, 60 s, 70 s, 80 s, 90 s, 100 s, 110 s, 120 s, 130 s, 140 s, 150 s, 160 s, 170 s, 180 s, 190 s, 200 s, 210 s, 220 s, 230 s, 240 s, 250 s, 260 s, 270 s, 280 s, 290 s, 300 s, 310 s, 320 s, 330 s, 340 s, 350 s, 360 s, 370 s, 380 s, 390s and 400 s, or any value within a range composed of any two of those point values; the detection time preferably is 20~250 s, more preferably is 60~210s. The continued reaction temperature is 60~160° C.; for example, the continued reaction temperature is any value among point values 60° C., 70° C., 80° C., 90° C., 100° C., 110° C., 120° C., 130° C., 140° C., 150° C. and 160° C., or any value within a range composed of any two of those point values, and preferably is 70~150° C. Thus, apparently that the reaction time is shortened significantly, and thereby the reaction efficiency is improved greatly.

In the present invention, to ensure a smooth and steady reaction, prevent a temperature or pressure out-of-control phenomenon, and improve safety of the production process while improving the transformation ratio of CHP and the yield of the phenol product, in the step (2), the preheating temperature in the preheating module is 60~160° C., and the preliminary reaction temperature in the mixing module is 60~160° C.

Preferably, the preheating temperature in the preheating module is 70~150° C.; the preliminary reaction temperature in the mixing module is 70~150° C.

In the present invention, a high-flux micro-channel reactor operating in a micro-channel continuous flow mode is employed to prepare phenol through acid catalytic decomposition of CHP. The reactor is assembled from multiple modules, which may be assembled in parallel or in series, and integrate the heat exchange passage and the reaction passage together. A thermocouple is provided in the heat exchange passage or heat conducting medium to measure the actual temperature of the heat transfer medium in the heat exchange passage or the external heat conducting medium. The modules may be made of monocrystalline silicon, special glass, ceramics, stainless steel coated with corrosion-resistant coating, metal alloy, or polytetrafluoroethylene, etc. For example, the special glass functional modules of the micro-channel reactor may be of a straight micro-channel structure, a heart-shaped mixed structure, a heart-shaped mixed structure followed by a straight micro-channel structure, or a capillary mixed structure followed by a straight micro-channel structure, etc.; the special glass functional modules of the micro-channel reactor include functional modules that have dual feed ports and a single discharge port and functional modules that have a single feed port and a single discharge port. The micro-channel reactor selected in the present invention has a safe operating temperature range of −25~200° C. and a safe operating pressure range of 0~18 bar, and the material pipe connections are made of perfluoroalkoxy resin (PFA) material. The reaction system may be corrosion-resistant and pressure-resistant, and the pressure resistance rating may vary, depending on the material.

In the present invention, to improve the transformation ratio of CHP and the yield of the phenol product, in the step (2), the preheating module is a straight micro-channel module, the mixing module is an enhanced heart-shaped micro-channel module, capillary microchannel module, or straight micro-channel module, and the mixing and reaction module group comprises a series of enhanced heart-shaped micro-channel modules, a combination of a series of enhanced heart-shaped micro-channel modules and straight micro-channel modules, or a combination of a series of capillary microchannel modules and straight micro-channel modules.

According to the present invention, the number of the mixing and reaction module groups is determined according to the flow rate and the detention time for reaction.

According to the present invention, efficient mass transfer and heat transfer of the materials in the micro-channel are required. In the micro-channel structures of the modules, the hydraulic diameter of the micro-channels is 0.5~10 mm; for example, the hydraulic diameter may be any value among point values 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm and 10 mm, or any value within a range composed of any two of those point values.

In summary, phenol is prepared in a micro-channel reactor in the present invention, through a process consisting of material heat exchange procedure, mixing procedure, and CHP decomposition reaction procedure. Therefore, a raw material preheating module, a mixing module, and a number of reaction modules are designed, and the reaction time is shortened from tens of minutes to a range of tens of seconds to several minutes; thus, the reaction efficiency is improved significantly; in addition, the reaction is smooth and steady, the temperature and pressure are controlled, and the potential safety hazards in the existing processes are avoided; besides, the hold-up liquid in the equipment is reduced from several cubic meters in a conventional reactor to a range of tens of milliliters to hundreds of milliliters, the operation flow is simplified, and additional devices required in conventional intermittent operation are omitted.

Hereunder the present invention will be detailed in examples. In the following examples, the transformation ratio of CHP is measured by titration with an iodometric method, and the selectivity of phenol and the total yield of the product are measured by gas chromatography and liquid chromatography.

Unless otherwise specified, all raw materials are commercially available products.

EXAMPLE 1

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

Figure 1:
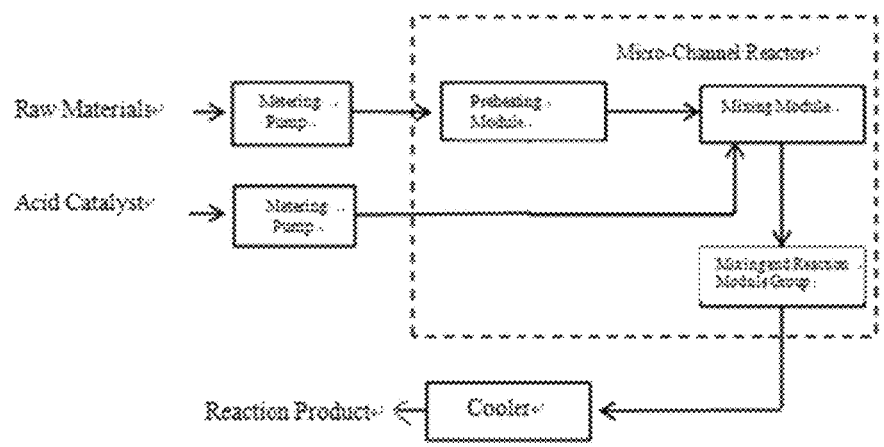
FIG. 1 is a reaction process flowchart of phenol preparation through acid catalytic decomposition of CHP according to the present invention.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 80° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 80° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 100%, the phenol selectivity is 99.8%, and the total yield of the product is 99.8%.

EXAMPLE 2

1. High-flux micro-channel reactor: As shown in FIG. 3, the high-flux micro-channel reactor comprises a preheating module (a straight micro-channel module 7), a mixing module (a straight micro-channel module 11), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 3, the method includes the following steps:

(1) CHP solution at 39% mass concentration and sulfuric acid at 35% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 80° C.; the sulfuric acid is pumped with the metering pump 4 into the enhanced heart-shaped micro-channel module 11 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 210 s, and the continued reaction temperature is set to 80° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 99.8%, the phenol selectivity is 99.7%, and the total yield of the product is 99.5%.

EXAMPLE 3

1. High-flux micro-channel reactor: As shown in FIG. 4, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules and straight micro-channel modules 12), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 4, the method includes the following steps:

(1) CHP solution at 15% mass concentration and sulfuric acid at 1% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules and straight micro-channel modules 12 for further reaction, the detention time for reaction is set to 120 s, and the continued reaction temperature is set to 90° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 96%, the phenol selectivity is 97.2%, and the total yield of the product is 93.3%.

EXAMPLE 4

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 48% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 90° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 95.4%, the phenol selectivity is 99.8%, and the total yield of the product is 95.2%.

EXAMPLE 5

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 80° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 10 s, and the continued reaction temperature is set to 80° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 97.8%, the phenol selectivity is 99.9%, and the total yield of the product is 97.7%.

EXAMPLE 6

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 250 s, and the continued reaction temperature is set to 90° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 100%, the phenol selectivity is 94.5%, and the total yield of the product is 94.5%.

EXAMPLE 7

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 60° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 97.2%, the phenol selectivity is 92.5%, and the total yield of the product is 89.9%.

EXAMPLE 8

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=360:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 20 s, and the continued reaction temperature is set to 160° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 100%, the phenol selectivity is 98.2%, and the total yield of the product is 98.2%.

EXAMPLE 9

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=100:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 80° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 100%, the phenol selectivity is 93.6%, and the total yield of the product is 93.6%.

EXAMPLE 10

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=1,500:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 80° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 92.7%, the phenol selectivity is 97.6%, and the total yield of the product is 90.5%.

EXAMPLE 11

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and sulfuric acid at 2.5% molar concentration are prepared in feed tanks 1 and 2 respectively.

(2) The flow regulation of the metering pumps 3, 4 is set to: molar ratio of CHP:sulfuric acid=390:1, the CHP solution is pumped with the metering pump 3 into the straight micro-channel module 7 of the high-flux micro-channel reactor and is preheated, and the preheating temperature is controlled to be 70° C.; the sulfuric acid is pumped with the metering pump 4 into the enhanced heart-shaped micro-channel module 8 of the high-flux micro-channel reactor, reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 80° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 100%, the phenol selectivity is 99.9%, and the total yield of the product is 99.9%.

EXAMPLE 12

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and $ZnCl_2$/MCM-41 ($ZnCl_2$ borne on MCM-41) at 2% mass concentration are prepared in feed tanks 1 and 2 respectively.

(2) The flow regulation of the metering pumps 3, 4 is set to: mass ratio of CHP:$ZnCl_2$/MCM-41=50:1, the CHP solution is pumped with the metering pump 3 into the straight micro-channel module 7 of the high-flux micro-channel reactor and is preheated, and the preheating temperature is controlled to be 80° C.; the $ZnCl_2$/MCM-41 is pumped with the metering pump 4 into the enhanced heart-shaped micro-channel module 8 of the high-flux micro-channel reactor, and is preliminarily mixed with the CHP solution for reaction, at 100° C. preliminary reaction temperature; the mixed raw materials are fed into a series of enhanced heart-shaped micro-channel modules 9 for further reaction, the detention time for reaction is set to 150 s, and the continued reaction temperature is set to 100° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 98%, the phenol selectivity is 99.9%, and the total yield of the product is 98%.

EXAMPLE 13

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and $ZnCl_2$/MCM-41 ($ZnCl_2$ borne on MCM-41) at 15% mass concentration are prepared in feed tanks 1 and 2 respectively.

(2) The flow regulation of the metering pumps 3, 4 is set to: mass ratio of CHP:$ZnCl_2$/MCM-41=200:1, the CHP solution is pumped with the metering pump 3 into the straight micro-channel module 7 of the high-flux micro-channel reactor and is preheated, and the preheating temperature is controlled to be 80° C.; the $ZnCl_2$/MCM-41 is pumped with the metering pump 4 into the enhanced heart-shaped micro-channel module 8 of the high-flux micro-channel reactor, and is preliminarily mixed with the CHP solution for reaction, at 100° C. preliminary reaction temperature; the mixed raw materials are fed into a series of enhanced heart-shaped micro-channel modules 9 for further reaction, the detention time for reaction is set to 150 s, and the continued reaction temperature is set to 100° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 94%, the phenol selectivity is 96.5%, and the total yield of the product is 91%.

EXAMPLE 14

1. High-flux micro-channel reactor: As shown in FIG. 2, the high-flux micro-channel reactor comprises a preheating module (a straight micro-channel module 7), a mixing module (an enhanced heart-shaped micro-channel module 8), and mixing and reaction modules (a series of enhanced heart-shaped micro-channel modules 9), wherein, the number of the mixing and reaction module groups is determined according to the flow rate and detention time for reaction, and the heat transfer medium is heat transfer oil.

2. The method for preparing phenol utilizing a micro-channel reactor is used. As shown in FIGS. 1 and 2, the method includes the following steps:

(1) CHP solution at 39% mass concentration and solid super-acid $WO_3/ZrO^{2-}$—$Fe_2O_3$ at 10% mass concentration are prepared in feed tanks 1 and 2 respectively.

(2) The flow regulation of the metering pumps 3, 4 is set to: mass ratio of CHP:$WO_3/ZrO^{2-}$—$Fe_2O_3$=50:1, the CHP solution is pumped with the metering pump 3 into the straight micro-channel module 7 of the high-flux micro-channel reactor and is preheated, and the preheating temperature is controlled to be 80° C.; the $WO_3/ZrO^{2-}$—$Fe_2O_3$ is pumped with the metering pump 4 into the enhanced heart-shaped micro-channel module 8 of the high-flux micro-channel reactor, and is preliminarily mixed with the CHP solution for reaction, at 80° C. preliminary reaction temperature; the mixed raw materials are fed into a series of enhanced heart-shaped micro-channel modules 9 for further reaction, the detention time for reaction is set to 120 s, and the continued reaction temperature is set to 90° C.; the system pressure is monitored with pressure meters 5 and 6 in the entire process; thus, a reaction liquid is obtained; then, the reaction liquid is cooled, discharged as a highly dispersed phase from the high-flux micro-channel reactor in a continuous flow state, and collected in a reaction liquid reservoir 10.

(3) The product is analyzed by GC analysis, and the CHP is measured by titration with an iodometric method. The measured transformation ratio of CHP is 98%, the phenol selectivity is 99.9%, and the total yield of the product is 98%.

While the present invention is described above in detail in some preferred embodiments, the present invention is not limited to those embodiments. Various simple variations, including combinations of the technical features in any other appropriate way, can be made to the technical scheme of the present invention within the scope of the technical concept of the present invention, but such variations and combinations shall be deemed as disclosed content in the present invention and falling in the protection scope of the present invention.

The invention claimed is:

1. A method for preparing phenol, comprising the following steps:
   (1) mixing cumene hydroperoxide and liquid acid or solid acid with a solvent to form a homogeneous solution or uniformly dispersed system;
   (2) loading the homogeneous solution or uniformly dispersed system of cumene hydroperoxide with a homogeneous solution or uniformly dispersed system of acid into a preheating module and preheating in a micro-channel continuous flow mode, preliminarily mixing the preheated materials for reaction in a mixing module in a micro-channel continuous flow mode, and then further mixing the materials for reaction in a series of mixing and reaction module groups in a micro-channel continuous flow mode, to obtain phenol.

2. The method for preparing phenol according to claim 1, wherein, in the step (1), in the homogeneous solution or uniformly dispersed system of cumene hydroperoxide, the mass concentration of cumene hydroperoxide is 10~60%.

3. The method for preparing phenol according to claim 2, wherein, the mass concentration of cumene hydroperoxide is 15~48%.

4. The method for preparing phenol according to claim 1, wherein, the cumene hydroperoxide is cumene oxidation liquid or concentrated cumene hydroperoxide at 80% or higher concentration.

5. The method for preparing phenol according to claim 1, wherein, in the step (1), in the homogeneous solution or uniformly dispersed system of acid, the molar concentration of the liquid acid is 1~35%, or the mass concentration of the solid acid is 2~15%.

6. The method for preparing phenol according to claim 5, wherein, the molar concentration of the liquid acid is 1.5~25%.

7. The method for preparing phenol according to claim 1, wherein, the liquid acid is at least one of sulfuric acid, methanesulfonic acid, and trifluoromethanesulfonic acid.

8. The method for preparing phenol according to claim 1, wherein, the solid acid is a solid super-acid and/or zeolite.

9. The method for preparing phenol according to claim 1, wherein, in the step (1), the solvent is acetone and/or cumene.

10. The method for preparing phenol according to claim 1, wherein, in the step (2), the molar ratio of cumene hydroperoxide to liquid acid is 100~1,500:1, or the mass ratio of cumene hydroperoxide to solid acid is 50~200:1.

11. The method for preparing phenol according to claim 10, wherein, the molar ratio of cumene hydroperoxide to liquid acid is 200~1,000:1.

12. The method for preparing phenol according to claim 1, wherein, in the step (2), in the mixing and reaction in the mixing and reaction module groups, the detention time of the materials is controlled to be 10~400 s, and the continued reaction temperature is 60~160° C.

13. The method for preparing phenol according to claim 12, wherein, the detention time of the materials is controlled to be 20~250 s, and the continued reaction temperature is 70~150° C.

14. The method for preparing phenol according to claim 1, wherein, in the step (2), the preheating temperature in the preheating module is 60~160° C., and the preliminary reaction temperature in the mixing module is 60~160° C.

15. The method for preparing phenol according to claim 14, wherein, the preheating temperature in the preheating module is 70~150° C., and the preliminary reaction temperature in the mixing module is 70~150° C.

16. The method for preparing phenol according to claim 12, wherein, the preheating temperature, reaction temperature, and continued reaction temperature are controlled via an external heat exchanger.

17. The method for preparing phenol according to claim 16, wherein, the heat transfer medium in the external heat exchanger is heat transfer oil, water, CHP solution to be preheated, or another material to be heated.

18. The method for preparing phenol according to claim 1, wherein, in the step (2), the preheating module is a straight micro-channel module, the mixing module is an enhanced heart-shaped micro-channel module, capillary micro-channel module, or straight micro-channel module, the mixing and reaction module group comprises a combination of a series of enhanced heart-shaped micro-channel modules connected in series or in parallel, a combination of a series of enhanced heart-shaped micro-channel modules and straight micro-channel modules connected in series or in parallel, or a combination of a series of capillary micro-channel modules and straight micro-channel modules connected in series or in parallel.

19. The method for preparing phenol according to claim 1, wherein, the number of the mixing and reaction module groups is determined according to flow rate and detention time for reaction.

20. The method for preparing phenol according to claim 1, wherein, in each module, the hydraulic diameter of the micro-channels are 0.5~10 mm.

* * * * *